United States Patent [19]
Motamedi et al.

[11] Patent Number: 6,143,019
[45] Date of Patent: Nov. 7, 2000

[54] METHOD FOR EMITTING THERAPEUTIC ENERGY WITHIN TISSUE

[75] Inventors: Massoud Motamedi, League City; David L. Ware, Galveston, both of Tex.

[73] Assignee: Board of Regents, The University of Texas System, Austin, Tex.

[21] Appl. No.: 09/026,590

[22] Filed: Feb. 20, 1998

Related U.S. Application Data

[63] Continuation-in-part of application No. PCT/US96/13396, Aug. 22, 1996, which is a continuation of application No. 08/517,961, Aug. 22, 1995, Pat. No. 5,824,005.

[51] Int. Cl.$^7$ .................................................. A61N 5/067
[52] U.S. Cl. ........................... 607/89; 607/99; 607/113; 607/122; 128/898; 606/15; 606/33
[58] Field of Search ............................. 607/88, 89, 92, 607/99–102, 105, 113, 122, 126; 606/14, 15, 33; 128/898

[56] References Cited

U.S. PATENT DOCUMENTS

| | | | |
|---|---|---|---|
| 4,785,815 | 11/1988 | Cohen ................................. | 128/642 |
| 4,862,887 | 9/1989 | Weber et al. ...................... | 128/303.1 |
| 4,985,028 | 1/1991 | Isner et al. ........................ | 606/15 |
| 5,104,393 | 4/1992 | Isner et al. ........................ | 606/15 |
| 5,154,501 | 10/1992 | Svenson et al. ................... | 128/419 D |
| 5,169,396 | 12/1992 | Dowlatshahi et al. ............. | 606/15 |
| 5,172,699 | 12/1992 | Svenson et al. ................... | 128/705 |
| 5,188,634 | 2/1993 | Hussein et al. .................... | 606/14 |
| 5,222,953 | 6/1993 | Dowlatshahi ....................... | 606/15 |
| 5,242,438 | 9/1993 | Saadatmanesh et al. .......... | 606/15 |
| 5,253,312 | 10/1993 | Payne et al. ....................... | 385/31 |
| 5,269,777 | 12/1993 | Doiron et al. ..................... | 606/7 |
| 5,298,026 | 3/1994 | Chang ................................. | 606/15 |
| 5,304,173 | 4/1994 | Kittrell et al. ..................... | 606/15 |
| 5,403,311 | 4/1995 | Abele et al. ....................... | 606/49 |
| 5,431,647 | 7/1995 | Purcell, Jr. et al. ............... | 606/16 |
| 5,431,649 | 7/1995 | Mulier et al. ...................... | 606/41 |
| 5,486,208 | 1/1996 | Ginsberg ............................ | 607/113 |
| 5,551,427 | 9/1996 | Altman .............................. | 128/642 |
| 5,643,253 | 7/1997 | Baxter et al. ...................... | 606/17 |
| 5,775,338 | 7/1998 | Hastings ............................ | 128/898 |

FOREIGN PATENT DOCUMENTS

| | | |
|---|---|---|
| 0283661 | 9/1988 | European Pat. Off. . |
| 0515867 | 12/1992 | European Pat. Off. . |
| 2 560 052 | 7/1990 | France . |
| 3911796 | 10/1990 | Germany . |
| 2006231 | 1/1994 | Russian Federation ................. 607/89 |
| 1604383 | 8/1985 | U.S.S.R. . |
| 1754128 | 8/1992 | U.S.S.R. ................................. 607/89 |
| WO 92/10142 | 6/1992 | WIPO . |
| 9325273 | 12/1993 | WIPO . |
| 9402077 | 2/1994 | WIPO . |

OTHER PUBLICATIONS

AngeLase, Inc. announcement for investigational use only.
Avitall, B. et al., "Physics and Engineering of Transcatheter Cardiac Tissue Ablation," *JACC*, vol. 22, No. 3, 921–32 (1993).

(List continued on next page.)

*Primary Examiner*—Lee Cohen
*Attorney, Agent, or Firm*—Thomas J. Engellenner; Scott D. Rothenberger; Nutter, McClennen & Fish, LLP

[57] ABSTRACT

A catheter capable of both sensing myocardial electrical activity and delivering ablating energy within myocardial tissue is disclosed. The catheter comprises electrodes on the outer sheath and contains a movable fiber optic cable that can be percutaneously advanced beyond the catheter body and into the myocardium for myocardial heating and coagulation, or modification of tissues responsible for cardiac arrhythmias. The fiber optic tip is designed to diffuse ablating energy radially to ablate a larger volume of tissue than is possible with a bare fiber optic tip. In addition, the tip is treated so that energy is not propagated in a forward direction, thus helping to prevent unwanted perforation of the heart tissue. Also disclosed is a method of cardioprotection from ischemia comprising inducing local hyperthermia in heart tissue.

16 Claims, 7 Drawing Sheets

OTHER PUBLICATIONS

Bashir, Y. et al., "Radiofrequency Current Delivery by Way of a Bipolar Tricuspid Annulus–Mitral Annulus Electrode Configuration for Ablation of Posteroseptal Accessory Pathways," *JACC*, vol. 22, No. 2, 550–6 (1993).

Blouin, L. and Marcus F., "The Effect of Electrode Design on the Efficiency of Delivery of Radiofrequency Energy to Cardiac Tissue in Vitro," *PACE*, vol. 12, part 2, 136–43 (1989).

Curtis, A., "Modification of Atrioventricular Conduction Using a Combined Laser–Electrode Catheter," *PACE*, vol. 17, part 1, 337–48 (1994).

Jackman, W. et al., "New Catheter Technique for Recording Left Free–Wall Accessory Atrioventricular Pathway Activation," *Circulation*, vol. 78, No. 3, 598–611 (1988).

Morady, F. et al., "Catheter Ablation of Ventricular Tachycardia with Intracardiac Shocks: Results in 33 Patients," *Circulation*, vol. 75, No. 5, 1037–49 (1987).

Morady, F. et al., "Radiofrequency Catheter Ablation of Ventricular Tachycardia in Patients with Coronary Artery Disease," *Circulation*, vol. 87, No. 2, 363–72 (ed. comment: Dubuc et al. 649–51) (1993).

Svenson, R. et al., "Laser Modification of the Myocardium for the Treatment of Cardiac Arrhythmias: Background, Current Results, and Future Possibilities," 327–46.

Weber, H. et al., "Percutaneous Nd:YAG Laser Coagulation of Ventricular Myocardium in Dogs Using a Special Electrode Laser Catheter," *PACE*, vol. 12, 899–910 (1989).

METHOD FOR EMITTING THERAPEUTIC ENERGY WITHIN TISSUE

The present application is a continuation-in-part of PCT Application No. PCT/US96/13396 which is a continuation of copending U.S. application Ser. No. 08/517,961, filed Aug. 22, 1995, now U.S. Pat. No. 5,824,005.

BACKGROUND OF THE INVENTION

1. Field of the Invention

The present invention relates generally to the field of medical apparatus and instrumentation and more particularly to the field of non-pharmacologic treatment of cardiac disorders including arrhythmias and ischemias, including percutaneous treatment, with specific application to the ablation or modification of tissues responsible for the arrhythmia, and for protection of ischemia reperfusion injury by application of local hyperthermal treatment.

2. Description of the Related Art

Cardiac arrhythmias arise when the rhythmic electrical signal from the heart's intrinsic pacemakers is not correctly propagated throughout the heart. A particular type of cardiac arrhythmia is a ventricular tachycardia, in which an ectopic focus occurs in the ventricle of the heart resulting in a heartbeat of over 100 beats per minute. This problem often occurs near a site of damaged myocardial tissue caused by an infarction or other injury.

Heating and thus coagulating ("ablating") myocardial tissues responsible for cardiac arrhythmias has been shown to be of great therapeutic value and is frequently done percutaneously ("catheter ablation"). By far the most common method involves delivering radiofrequency energy (RF) via a catheter with a flexible tip equipped with electrodes for sensing ("mapping") the endocardial electrical activation sequence, and for delivering RF energy or laser energy (see Svenson et al., U.S. Pat. No. 5,172,699). The arrhythmias which respond best to this therapy (with a >90% cure rate) are supraventricular. This is due (1) to well-defined mapping criteria highly predictive of cure and (2) to the small volume of tissue which, when ablated, prevents recurrent arrhythmia. Thus only few, or sometimes one, relatively superficial but well targeted, RF-induced lesion(s) may be necessary for success.

This same approach has been far less successful in treating the ventricular arrhythmias typically originating from tissues damaged by myocardial infarction. RF catheter ablation can be recommended only as adjunctive (not "first line") therapy for these arrhythmias. Reasons for this, again, are (1) mapping criteria which are not as clearly correlated with success as in the case of supraventricular arrhythmias and (2) larger tissue volume responsible for the arrhythmia.

An attempt to address the problem of ventricular arrhythmias is described by Isner and Clarke, U.S. Pat. No. 5,104, 393, which discloses a catheter for ablation of cardiac tissue. The instrument tip is held in place in the endocardium by a fixation wire, with the ablation tip held on the endocardial wall, and thus, the tip does not directly reach deep intramyocardial tissue where arrhythmias may arise. Other present methods are similarly inadequate for ablating such deep tissue, precluding percutaneous treatment for many patients.

In recent years there has been significant interest in generating elevated levels of heat shock proteins (HSP's) in the heart and examining their cardioprotective abilities. These efforts have led to the development of experimental protocols in which different stresses such as hypoxia, mechanical strain, hemodynamic overload and hypothermia have been used to express HSP's (especially the HSP70 family) and examine the subsequent protection to the heart from ischemia/reperfusion (I/R) injury.

Previous work in various in-vitro and in vivo animal models has shown that hyperthermia-induced expression of HSP's is accompanied by protection against ischemia/reperfusion (I/R) injury of the heart (Marber et al. 1993; Donnely et al. 1992; Yellon et al. 1992; Walker et al. 1993; Currie et al. 1993). This protection has not only been shown to be related to HSP expression but also directly correlated to the amount of HSP induced before I/R (Hutter et al. 1994). Additionally, expression of HSP's as a result of heat shock response has been shown to improve functional recovery after ischemia and reperfusion (Currie et al. 1988).

In previous hyperthermia studies HSP expression was achieved by either heating the buffer solutions of in vitro isolated hearts or by subjecting animals to whole body hyperthermia 24 hours before I/R. However, whole body heat stress may exert negative effects on extracardiac cells such as blood cells, as the observed duration of cardioprotection in animals treated with whole body hyperthermia in vivo is less than cardioprotection of hearts heat shocked during isolated buffer perfusion in vitro. Walker et al. demonstrated these extracardiac effects in experiments in which buffer perfused hearts and blood (non-heat shock) perfused hearts of animals subjected to whole body hyperthermia were able to withstand longer periods of ischemia than animals subjected to whole body hyperthermia whose hearts were still perfused by the heat shocked blood components.

Their is a need therefore for a method of directly heating the heart and inducing regional HSP expression, thus avoiding limitations that may be induced during whole body hyperthermia.

SUMMARY OF THE INVENTION

The present invention addresses the problems described above by (1) delivering laser light or other ablating energy intramyocardially, and (2) diffusing the ablating energy over a broad area in the myocardium without causing excess heat on the endocardial surface or in the blood pool. Mapping of the site of the arrhythmia is made possible by electrodes provided on the catheter sheath that may be switchably connected to a physiological recorder. In a particular embodiment, mapping electrodes may be provided on the retractable tip, in order to more precisely define the area of myocardium in which the arrhythmia arises. The catheter is controllably flexible for placing the electrodes in the correct position for contacting and treating the desired area.

The present invention thus provides instruments and methods for percutaneous catheter ablation of larger myocardial lesions than have previously been possible, by the intramyocardial delivery of diffused laser light, or other ablating energy, thus enhancing the potential for cure of ventricular arrhythmias, for example. Patients may therefore not require pharmacological or surgical therapy, reducing the morbidity and expense of therapy.

The invention, in certain aspects, may be described as an apparatus for endocardial insertion comprising a catheter adapted to access the cardiovascular system. An energy transmitting conductor extends along and within the catheter and has a tip which is extensible beyond the distal end of the catheter and also retractable within the catheter. The conductor may be a conductor for electrical current, ultrasound, microwave, an optical wave guide such as a wave guide for coherent light or a conduit for liquid and most preferably comprises an optical fiber.

The tip of the conductor is configured to penetrate cardiac tissue (i.e. through the endocardium and into the myocardial tissue) and to direct energy from and radially and/or axially relative to the conductor when the conductor is extended beyond the distal end of the catheter and into the myocardial tissue. The tip may form a pointed end, in order to more easily penetrate the endocardium, or the tip may form a flat end, a flat elliptical end or other appropriate configuration. Exemplary tips are described in U.S. Pat. No. 5,253,312, or U.S. Pat. No. 5,269,777 incorporated herein by reference. A preferred tip is the diffusing laser tip available from Rare Earth Medical Lasers Inc., Dennis, Mass. The end of the tip may also be coated or coupled with an energy or light reflecting or deflecting material in order to prevent forward propagation of the ablating energy. This feature increases the safety of the present invention by helping to prevent unwanted perforation of cardiac tissue.

The apparatus may also have one or more electrodes positioned near the distal end of the catheter and may preferably have an electrode pair positioned at the distal end of the catheter to be used to accurately map the arrhythmia. Alternatively, the apparatus may even provide one or more electrodes positioned on the retractable tip for interstitial mapping. Additional electrodes may be positioned on a probe that may be advanced from the end of the catheter into the tissue for recording intramyocardial electrical activity. It is understood that the conductor for the mapping electrodes is preferably incorporated into the sheath of the catheter. However, in those embodiments in which a mapping probe is extensible beyond the catheter sheath, a conductor may pass through the lumen of the catheter in addition to the conductor of ablating energy. Apparatus and methods for stimulating, pacing, and endocardial mapping of arrhythmias are well known in the art, and they are not, in and of themselves, considered to constitute the present invention. The overall apparatus will preferably include a physiological recorder switchably connected to at least one of the electrodes operable to map local cardiac electrical activity and may further comprise an electrical stimulating device switchably connected to at least one of the electrodes operable to pace or otherwise stimulate the heart tissue. The pacing electrodes may be used to induce or to terminate arrhythmias during the procedure. The apparatus may further comprise a stabilizer, or stabilizing device to help prevent unwanted penetration of heart tissue. The stabilizer is exemplified by, but is not limited to, an inflatable, doughnut-shaped balloon that expands radially and may expand distally relative to the catheter. The stabilizer may be positioned on the outer surface of the catheter to stabilize the catheter within a body organ or cavity. Other stabilizers may include, but are not limited to disk or basket shaped extensions which are attached to the catheter's distal tip.

The present invention may also be described as a maneuverable catheter for ablation of cardiac tissue, where the catheter has a retractable tip, and the tip is extendible into the myocardium tissue for lateral diffusion of ablating energy into the intramyocardial tissue. The ablating energy may be provided in the form of laser energy, radiofrequency energy, microwave, ultrasound or a medium such as hot water, and is preferably 400 to 3,000 nm wavelength laser energy.

A certain aspect of the present invention resides in a method of treating cardiac arrhythmia which comprises the steps of positioning the distal end of an apparatus as described above on the endocardium, identifying the tissue involved in the arrhythmia, extending the distal end of the conductor past the distal end of the catheter and into the tissue, and transmitting ablating energy through the conductor into the tissue. In the practice of this method, the conductor may be a waveguide and the ablating energy may be laser energy. The distal end of the waveguide preferably comprises a penetrating tip and means for distributing laser energy into the selected tissue in a desired pattern, which may be a uniform distribution extending radially from the waveguide.

In certain embodiments, the present invention may be described as a method for promoting myocardial revascularization, through a process called angiogenesis. In the preferred method of practicing this embodiment, the tissues are heated to about 40° C. by introducing the catheter tip into the myocardium which has been previously identified as being underperfused with blood (i.e., ischemic). The procedure would be performed in a manner similar to that described for the treatment of arrhythmias, except in most cases it would be performed intraoperatively and involve a larger volume of tissue.

As shown herein, the protective effect of local hyperthermia may be due to the induction of heat shock proteins. Since heat shock proteins (HSP) are a non-specific response to injury, it is contemplated that other mechanical, thermal, optical, electrical and photochemical means may be used to induce HSP locally in the heart. Therefore any device that may deliver any of such types of energy to the area of the heart may be used to induce local injury in the heart tissue thus elevating HSP and other substances that could have protective effects. However, it is contemplated that local irradiation and/or heating may provide a the safest and most preferred approach to local elevation of HSP in the heart. Local temperature elevation in myocardial tissue can be realized by heating from the epicardial surface, endocardial surface, interstitial heating or a combination of these modalities.

In the practice of the method, devices emitting laser, ultrasound, microwave, radiofrequency or conductive heat as from a hot tip may be used to heat the heart tissue. These devices may, by way of example only, be placed in a blood vessel, they may be introduced through a natural opening such as an esophagus to irradiate and/or heat the heart via radiative or conductive heating with or without simultaneous cooling or by opening a small port between the ribs and performing thoroscopy for treatment of patients with chronic ischemic heart, for example. Such treatment may be administered as a single application, or every 2 to 3 days for a period of time necessary to have a beneficial effect as determined by the practitioner. Such treatments may be administered for protection of transplant, bypass or other patients, including for example patients receiving transplanted organs other than a heart such as a kidney, for example.

The present invention may then be described in certain embodiments as an apparatus for inducing hyperthermic, coagualative or photochemical processes in cardiac tissue. The apparatus would include a catheter adapted to access the cardiovascular system and a conductor extending along and within the lumen of the catheter for transmitting energy to the distal end of the catheter. The conductor preferably has a distal end which is extensible beyond the distal end of the catheter and there is also included an energy source in communication with the proximal end of the conductor effective to transmit energy through the conductor and into a tissue in contact with the conductor to increase the temperature of the tissue above 37° C. in order to modulate biological responses and promote tissue angiogensis and/or tissue protection. As is well known in the art, such a method is a time and temperature dependent process so that more or less energy may be applied over a longer or shorter period of time to achieve the same effect. However, any such use of an instrument to increase the temperature to a level that will induce endogenous protective mechanisms such as heat shock proteins or growth factors is encompassed by the spirit and scope of the present claimed invention. Preferred energy sources for the practice of this embodiment include, but are not limited to light, microwave, heated liquid, ultrasound, radiofrequency, or direct current energy, and the light energy may be laser, ultraviolet, visible or infrared light energy.

The present invention may also be described in certain embodiments as a method of inhibiting tissue damage due to insults such as reperfusion injury comprising providing radiative or conductive energy to said tissue in an amount effective to induce local hyperthermia and facilitate endogenous expression of heat shock protein and growth factors. This method may be used in cardiac tissue or heart tissue through application of energy endocardial surface, the epicardial surface or interstitial area of the heart. The method may also be applied to other organs, particularly organs to be transplanted. This method would include heating the organ in vivo or in vitro for a desired time at sublethal temperature via heat conduction from the surface of the organ, or directly within the organ by using various sources of energy such as laser, ultrasound, microwave, electrical current or radiofrequency to stimulate the endogenous expression of proteins and structures such as heat shock proteins that are capable of providing additional means to protect the tissue and thus extend the time for tissue transplant and/or improve the outcome of organ transplant.

The invention may also be described in certain embodiments as a method of delivering light and/or heat to tissue in order to manipulate and/or modulate biological response and stimulate the endogenous expression and release of substances such as heat shock proteins and growth factors such as vascular endothelial growth factor (VEGF), for example. For example, a device that is used to deliver light superficially and/or interstitially for photodynamic processes that will lead to the induction of angiogensis or tissue protection in cardiac tissue with or without the use of an exogenous light activated substance that may facilitate the expression of such substances in cardiac tissue.

An embodiment of the present invention is also the use of interstitial illumination in combination with light activated substances that may induce heat shock protein and/or promote the growth factors. Optical and ultrasound energy may be introduced to activate exogenous substances that have been administered such as those known in the art to be effective in photodynamic therapy. It is contemplated that such use may induce a protective response in myocardial tissue as described herein.

As used herein, "ablate" means to thermally coagulate and/or remove the tissues where arrhythmias originate or through which arrhythmias are sustained, and in a more general sense, ablation means the desiccation of tissue by the application of heat. For example, an ablating energy would be one that would cause the tissue to reach a temperature of at least about 80–90° C. Hyperthermia is defined as a temperature above normal body temperature (37° C.), but usually less than the temperature necessary to cause tissue coagulation. Alternatively ablation may be achieved by selectively targeting cell surface proteins or gene loci for deactivation to affect electrical conduction without desiccating the target tissue. For example, ion channels responsible for cellular action potentials (e.g., potassium and sodium channels) and for intercellular communication (the conexins) may be influenced. Photodynamic therapy (PDT) with light activated substances (e.g. tagged antibodies or DNA) may be a preferred method for this type of ablation. Additionally, the tissue substrate for arrhythmia development may be favorably altered by reducing the development of myocyte hypertrophy and intercellular collagen, features of infarct healing and myocardial remodeling that induce myocardial dysfunction and increase the likelihood of life-threatening ventricular arrhythmias. It is contemplated that the present device may influence the degree of local hypertrophy and collagen formation (or collagen breakdown) by directly changing relevant proteins or their genetic expression. Finally, this device may be used to induced apoptosis in regions of local myocyte hypertrophy, such as occurs in the septum of patients with hypertrophic obstructive cardiomyopathy.

DETAILED DESCRIPTION OF THE PREFERRED EMBODIMENTS

In preferred embodiments, the present invention comprises a catheter capable of both sensing myocardial electrical activity and delivering laser light or other types of energy within myocardial tissue. The distal catheter comprises an outer sheath whereon electrodes are positioned and through which a movable fiber optic cable or other energy delivering device can be percutaneously advanced beyond the sheath and into the myocardium for intramyocardial heating and/or photocoagulation, or modification of tissues responsible for cardiac arrhythmias. Additional mapping data may be obtained by inserting electrodes along a probe into the myocardium, prior to exchanging the mapping probe for the ablating tip. The tip used for intramyocardial heating may be further designed to diffuse photons or other energy laterally, thereby heating larger volumes of tissue than is possible with current endocardial treatments. The tip is designed so that it does not allow forward irradiation, and thus prevents full-thickness ablation and perforation. The overall design of the invention is intended for percutaneous treatment of cardiac arrhythmias such as ventricular tachycardias, although the diffusing tip may also be used intraoperatively. Although treatment of ventricular tachycardia is the most preferred embodiment of treating arrhythmias, treatment of other arrhythmias may be accomplished with few or no modifications of the disclosed apparatus and methods. In addition, the treatment of ischemic heart conditions by hyperthermic induction of angiogenesis may be accomplished by the apparatus and methods of the present invention. It is understood and shown herein that local heating of heart tissue induces heat shock proteins that are cardioprotective in ischemia/reperfusion and the induction of heat shock proteins in heart tissue as described herein is an embodiment of the present invention.

Figure 1:
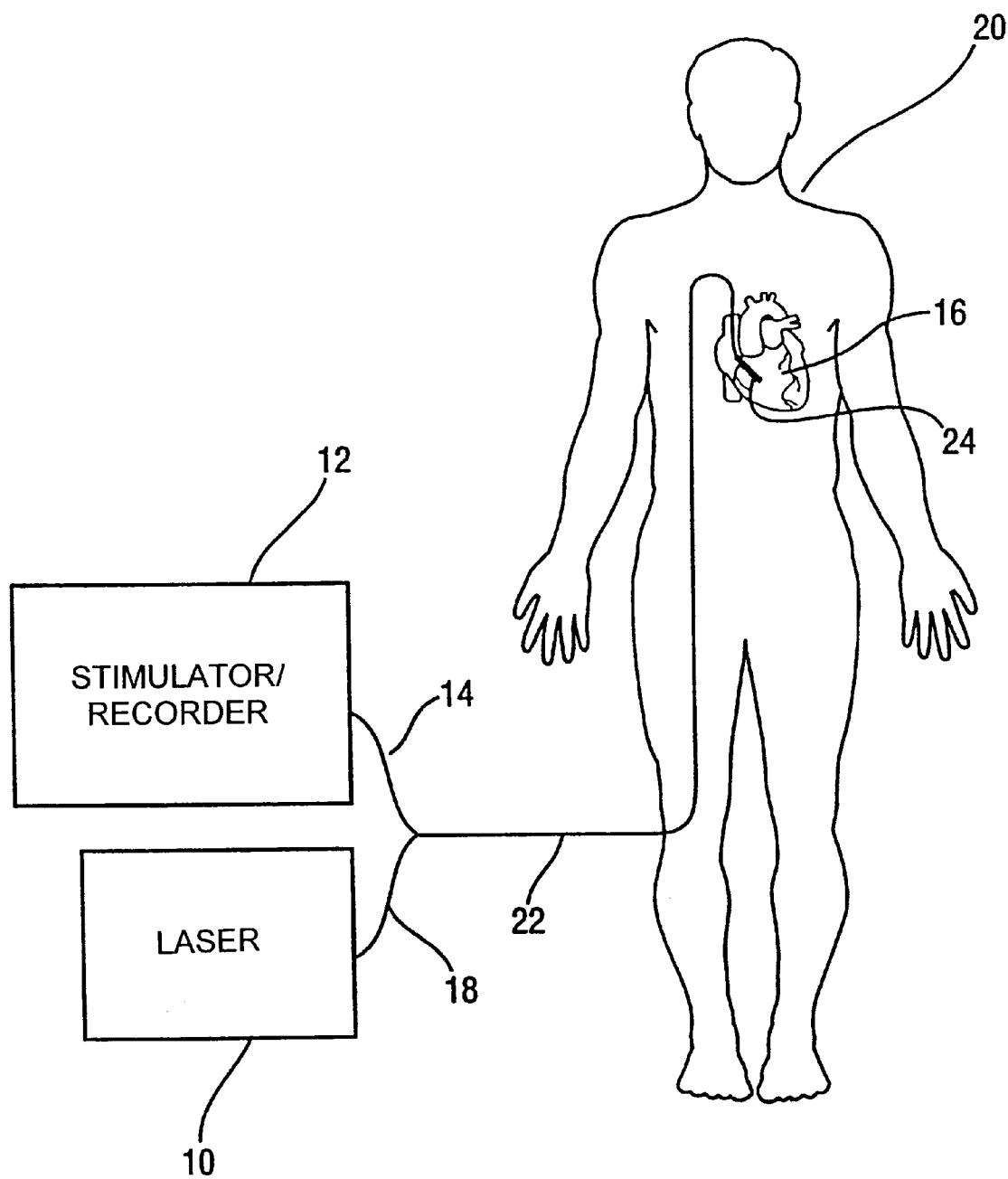
FIG. 1. A schematic of the laboratory arrangement necessary to perform the methods of intramyocardial catheter ablation.

FIG. 1 is a schematic diagram of a preferred embodiment of the present invention in use in a human patient 20. In this embodiment, an external laser source 10, is connected to the distal end 24 of a catheter 22 by a conductor 18 passing through the lumen 44 of the catheter 22 (See also FIG. 2). Also passing through the lumen 44 of the catheter 22 is a conductor 14, connected to a physiological recorder 12, and/or a stimulator 12. Alternatively, the conductor 14 may be incorporated into the sheath 36 of the outer catheter 22. In the embodiment shown in FIG. 1, the catheter 22, is inserted into a femoral artery (or vein), advanced into a chamber of the heart 16, and is placed in contact with the endocardium.

Figure 2:
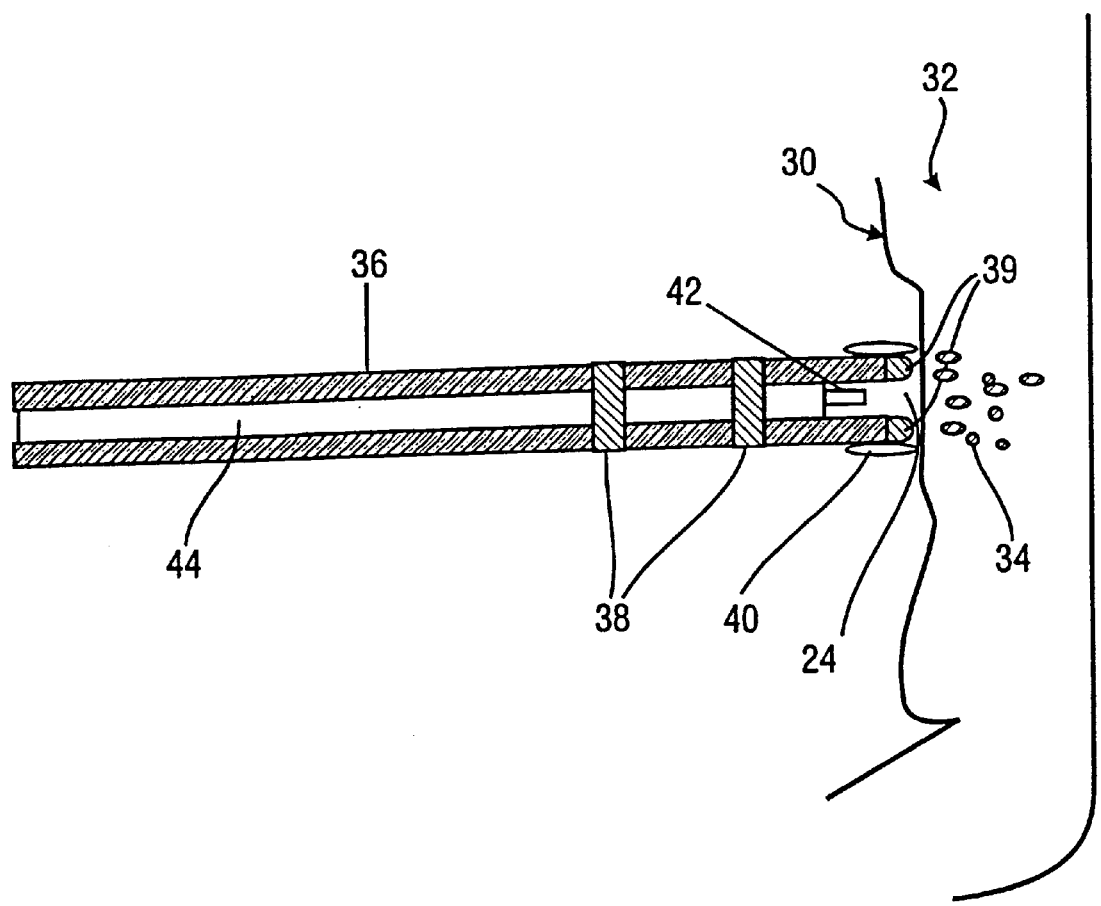
FIG. 2. A schematic drawing of the distal portion of the catheter, with the tip positioned against the ventricular endocardium during mapping, prior to advancement of the fiberoptic diffusion tip and delivery of laser light.

The distal portion of a catheter 22 is shown in FIG. 2. The distal end 24 of the catheter 22 is shown in position against the ventricular endocardium 30 as used during mapping, prior to advancement of the fiberoptic diffusion tip 42 into the interstitial tissue 32 and delivery of laser light into the arrhythmic zone 34. Attached to the catheter sheath 36, is a series of electrodes 38 that may be used for mapping, including one pair 39 positioned at the distal end 24 of the catheter 22. The pair of mapping electrodes 39 positioned at the distal end 24 sense electrical activity, and this information is used to find the arrhythmogenic focus 34 (i.e. the myocardial site giving rise to the arrhythmia). These electrodes 39 at the distal end 24 of the catheter 22 may also be used to pace the heart when pacing techniques are used to assist with mapping. A pair of proximal electrodes 38 positioned along the catheter sheath 36 may then be used to sense endocardial activity during pacing from the distal pair 39. Also shown is an inflatable, circular balloon 40 in the deflated state, ringing the outer surface of the distal end 24 of the catheter 22. The ablating probe tip 42 is retracted entirely within the lumen 44 of the catheter 22, in the unextended position.

Figure 3:
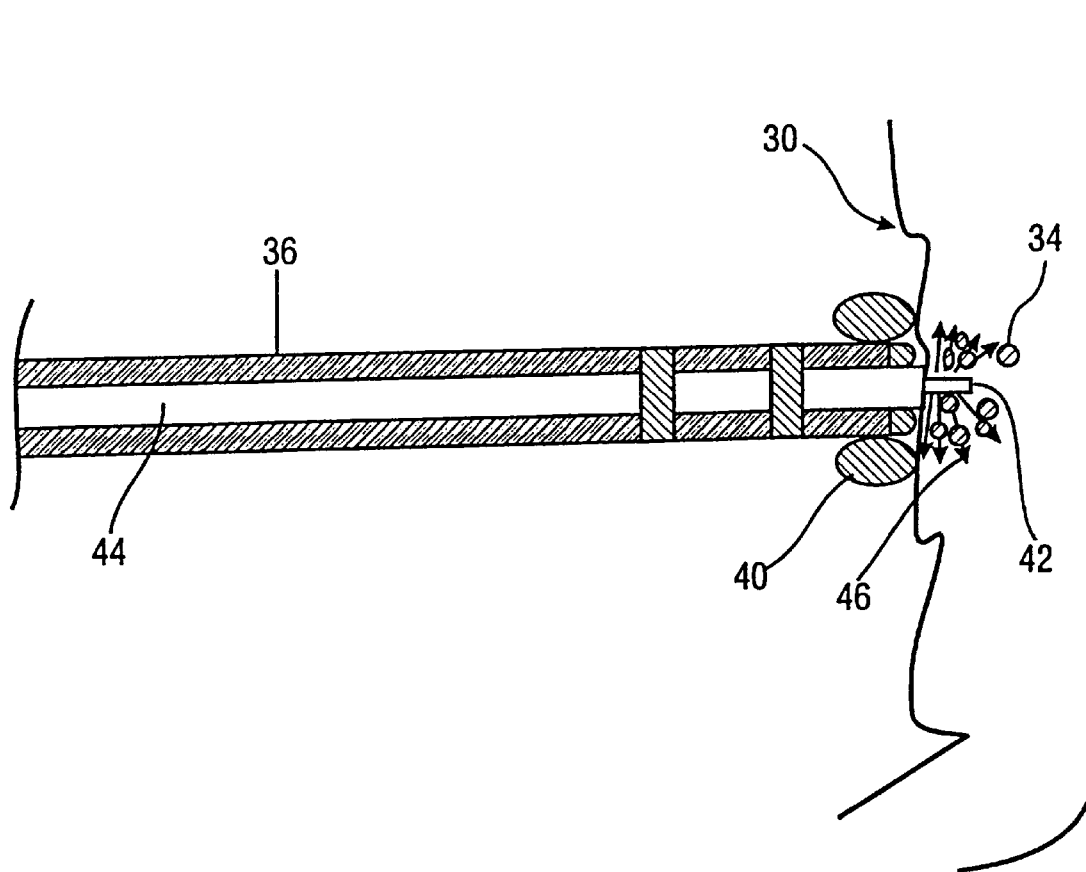
FIG. 3. The catheter of FIG. 2 in the irradiating position, with the penetrating optical fiber tip extended into the myocardium. A circumferential doughnut-shaped balloon has been inflated to help prevent further advancement of the entire catheter system and perforation of the ventricle.
Figure 4:
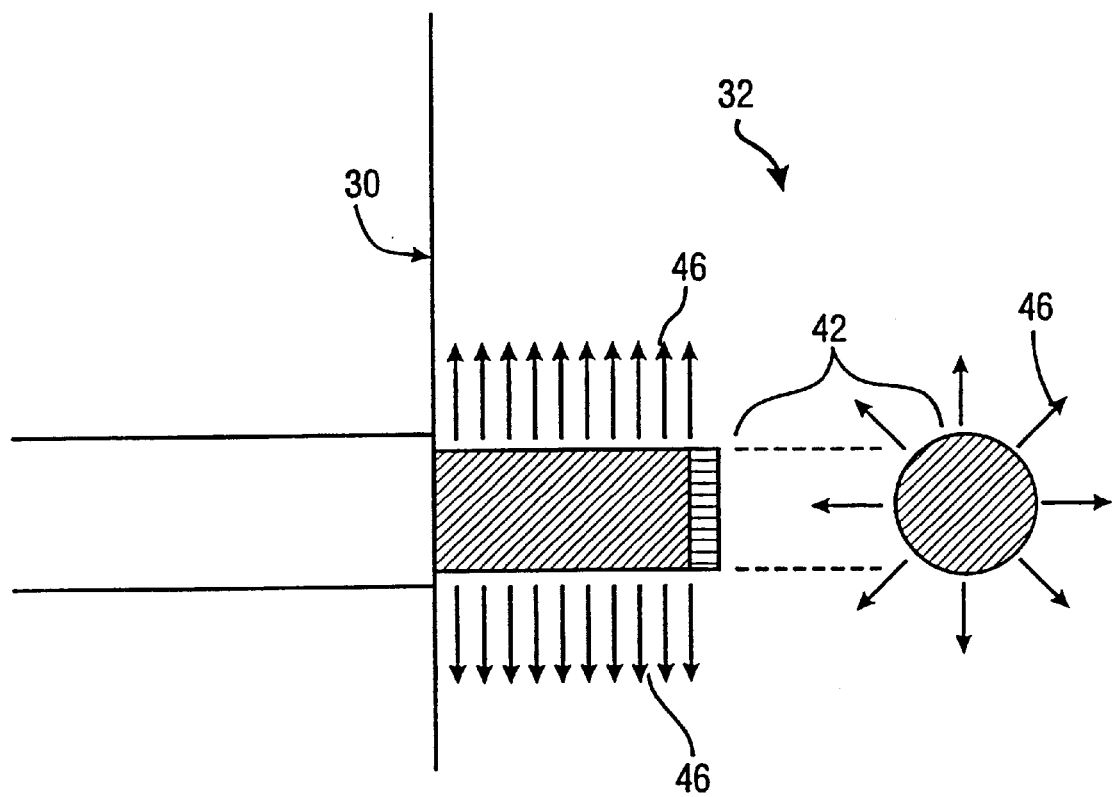
FIG. 4. Schematically depicts the diffusing optical tip and intramyocardial light distribution. The end of the fiber may be coated with or coupled to an optical element to deflect or reflect light so that no light is emitted in the forward direction relative to the tip to prevent perforation and/or damage to the epicardial coronary arteries or pericardium.

FIG. 3 is a schematic drawing of the catheter 22 in irradiating position. The ablating probe tip 42, is extended beyond the distal end 24 of the catheter 22 and placed intramyocardially for deep tissue coagulation of the arrhythmic zone 34. The stabilizing balloon 40, is shown in the inflated state which inhibits movement of the catheter tip 42 with respect to the heart tissue, and which helps prevent unwanted perforation of the heart tissue by the catheter tip 42. Ablating energy 46 is shown being delivered into the arrhythmic zone 34. FIG. 4 depicts the ablating probe tip 42, in side view and end view. The tip 42 extends from the endocardial wall 30, into the myocardium 32, and radially diffuses the ablating laser energy 46.

Figure 5:
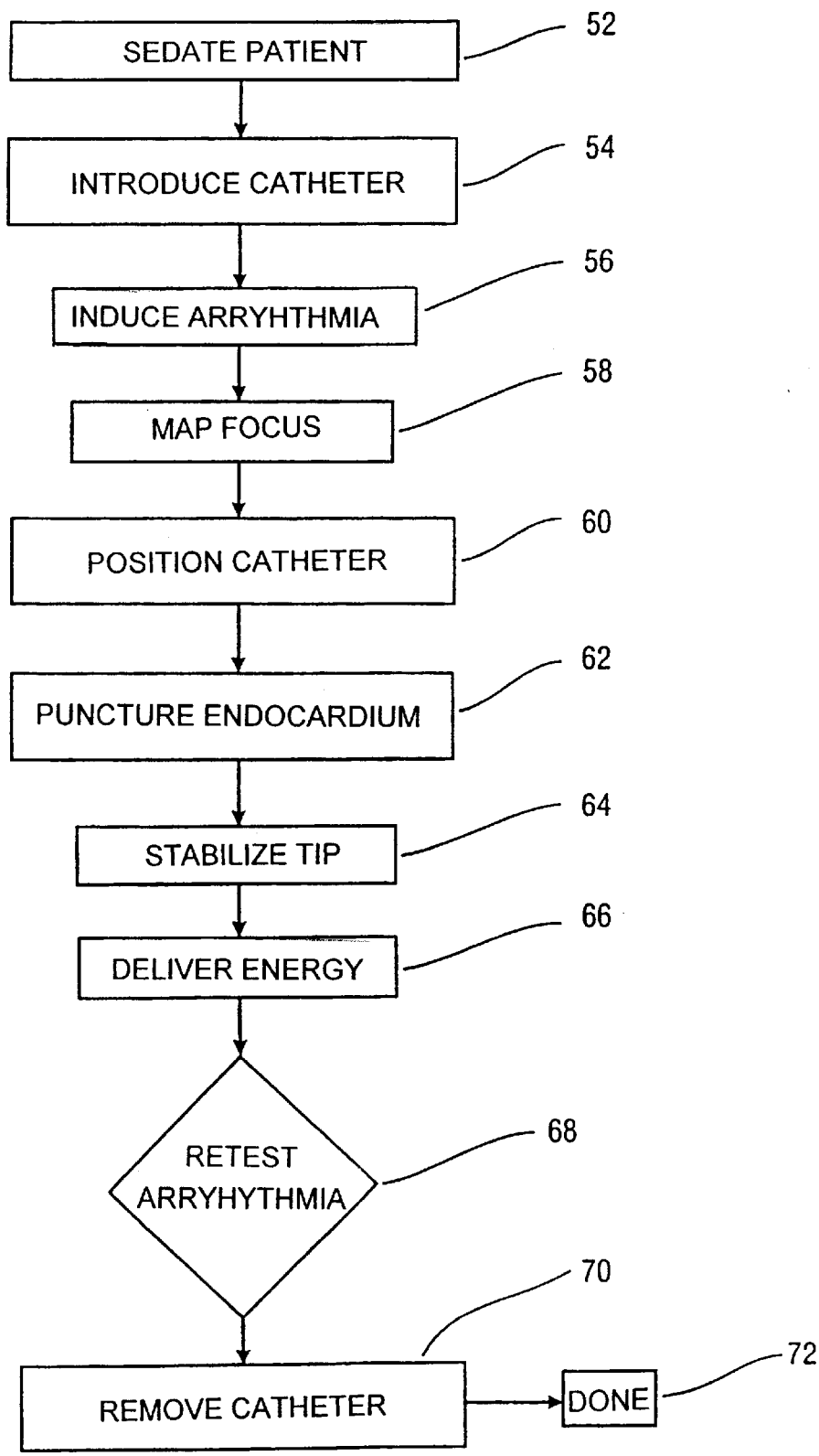
FIG. 5. A flow diagram of a typical method of use of the present invention.

FIG. 5 is a flow diagram of a typical method of use of the present invention, preferably in a human patient. The patient is sedated and instrumented in the standard fashion known to those of skill in the art 52. The catheter system is inserted into a major artery or vein and introduced into the selected heart chamber 54. In a preferred method of treating a ventricular tachycardia the catheter is inserted through the femoral artery. If the arrhythmia to be ablated is not ongoing, it is induced using standard pacing techniques known to those of skill in the art 56. The arrhythmic focus may be mapped 58 by percutaneously flexing the distal end 24 of the catheter 22 so that it contacts multiple endocardial sites, and observing electrical responses transmitted from the mapping electrodes connected to a physiological recorder. The distal end 24 of the catheter 22 is then positioned 60 at the endocardial surface 30 adjacent the arrhythmic zone.

When the distal end 24 of the catheter 22 is in the desired position, the tip 42 which may have a pointed end, for example, or may have a flat end, is extended past the catheter sheath 36 a predetermined distance, puncturing the endocardium 30 and extending 62 into the myocardial tissue 32. When the tip 42 is in position, the stabilizing device 40 is activated 64 to prevent perforation. Once in the irradiating position, the entire length of the diffusing component of the tip 42 is embedded below the endocardial surface 30 to avoid irradiating the endocardial surface 30 and the blood pool, thereby helping to prevent endocardial charring and coagulum formation. In certain preferred embodiments, the stabilizing device 40 comprises a balloon which may be inflated or deflated by percutaneously manipulating a handle at the catheter's 22 proximal end.

A predetermined amount of ablating energy 46 is then delivered 66 radially from the tip 42 into the myocardium 32. After delivery of ablation energy 46, an attempt is made to re-stimulate an arrhythmia 68. If needed, further ablating energy 46 is delivered. When no further treatment is necessary or desired, the apparatus is removed from the patient 70 and the procedure is complete 72.

The following examples are included to demonstrate preferred embodiments of the invention. It should be appreciated by those of skill in the art that the techniques disclosed in the examples which follow represent techniques discovered in connection with the invention to function well in the practice of the invention, and thus can be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

EXAMPLE 1

Ablation of Cardiac Tissue in Dogs

For preliminary data, three anesthetized mongrel dogs were used to place 23 intramyocardial lesions from the epicardial surface of the left ventricle (4–12 lesions per dog). The tip of the optical fiber was extended for 8 mm into the myocardium. Three to six Watts of laser energy (805 nm) were administered for 30–120 seconds. The dogs were euthanized and the cardiac tissue was examined. Lesions were from 5.3 to 10.5 mm wide and 7.7 to 12.6 mm deep. No tissue vaporization or marked charring was evident. These studies demonstrate that large but controlled lesions can be made with intramyocardial laser irradiation using the methods and apparatus of the present invention.

EXAMPLE 2

Laser Ablation Treatment of Ventricular Tachycardia in a Human Patient

In a preferred method of practicing the present invention, percutaneous ablation to treat a ventricular tachycardia in a human patient may proceed as follows: The patient, in the electrophysiology laboratory is sedated, instrumented and, with fluoroscopic guidance, the catheter (7 or 8 French) is guided to the heart through a large artery (FIG. 1), preferably through a femoral artery. Programmed stimulation (a standard technique known to those of skill in the art) induces the ventricular or supraventricular tachycardia and the operator "maps" its electrical activation sequence. Mapping is performed during sustained and hemodynamically stable ventricular tachycardia by percutaneously flexing the distal end 24 of the catheter 22 so that it contacts multiple endocardial sites. By sensing the electrical activity at various sites, the arrhythmic focus, or site of origin of the arrhythmia 34 is located.

During the mapping procedure the optical fiber tip 42 is retracted inside the catheter sheath 36 and the distal electrode pair 39 is placed in contact with the endocardium 30 (FIG. 2). The catheter 22 is steered percutaneously by flexing a handle attached to the proximal end of the catheter 22. A number of such handles are commercially available, with a preferred handle being manufactured by Cordis Webster, Inc. 4750 Littlejohn St., Baldwin Park, Calif. 91706. When the area of myocardium to be photocoagulated is located, the fiberoptic tip 42 (200–600 micron diameter) (Rare Earth, Dennis, Mass. or PDT Systems, Goleta, Calif.) is extended 3 to 5 mm from the distal end 24 of the mapping catheter 22, penetrating the endocardium 30 and extending into the target tissue 32 for deep tissue irradiation (FIG. 3). To prevent myocardial perforation, light does not exit from the distal end of the tip 42, but diffuses laterally into a broad area of myocardium (FIG. 4). It is also an aspect of the invention that the energy diffusing tip 42 is completely inserted into the interstitial tissue 32 so that ablating energy is not applied directly to the endocardial surface 30. As a consequence of this procedure the endocardial surface 30 is not charred and is disrupted only by the small puncture site; this is in contrast to the outcome of current treatments using RF and laser energy sources applied to the endocardial surface 30.

Once the tip 42 is in the irradiating position, a small balloon 40 encircling the distal end 24 of the catheter 22 is inflated to stabilize the catheter 22 and help prevent perforation of the heart tissue. Laser energy of 400 to 3,000 nm wavelength is then conducted from the source 10 to the tip 42 and dispersed radially by the tip for 30–120 seconds depending on the wavelength used and the size of lesion necessary to ablate the arrhythmic focus. After the delivery of laser energy, an attempt may be made to re-stimulate the arrhythmia. If the arrhythmia cannot be re-stimulated, the treatment ends and the catheter 22 is removed from the patient. If an arrhythmia is stimulated, then the physician may choose to map the arrhythmia and repeat the procedure.

The present invention may be applied in a similar fashion during arrhythmia surgery to ablate or modify arrhythmogenic myocardium, except the ablation proceeds during direct visualization of the heart. This approach may eliminate certain limitations associated with intraoperative cryoablation. If PDT is used (either during a catheter procedure or surgery) to selectively target proteins or gene loci, the above maneuvers would follow administration of the light activated substance.

EXAMPLE 3

Treatment to Induce Angiogenesis

In addition to modifying conduction pathways of the heart for the treatment of cardiac arrhythmias, energy delivery using the device disclosed herein has potential to increase myocardial perfusion in patients with coronary insufficiency. In previous attempts to address this problem, transmyocardial channels 1 mm in diameter have been produced using the high-power (800 Watt) $CO_2$ laser. It has been proposed that these channels convey oxygen rich blood directly to ischemic tissue. Preclinical and clinical results are promising, and the Food and Drug Administration has recently approved a Phase II trial.

However, the theory of revascularization mentioned in the previous paragraph has been challenged by pathological studies showing that laser-induced transmyocardial channels do not remain patent. Alternate theories propose that the improvement seen after this procedure is not due to direct myocardial revascularization, but results from secondary changes which occur during healing, in response to the transient rise in temperature (hyperthermia). There is evidence that hyperthermia provides a transient protective mechanism in the heart. During exposure to laser light, heat shock protein and free radical production may stimulate angiogenesis (the formation of new blood vessels) and improve tissue perfusion. Because the device disclosed herein is capable of intramyocardial heating, it is contemplated to be more effective in promoting angiogenesis than one which irradiates only the heart's surface. In addition, as a part of the present invention, one may induce local hyperthermia in the heart using a variety of methods and/or instruments.

An example of the benefits of local induction of hyperthermia in a rat model of ischemia/reperfusion is presented here. In this example, the possible extracardiac effects have been eliminated by demonstrating the ability to locally induce hyperthermia and expression of HSPs and subsequently provide protection against 30 minutes of ischemia and 120 minutes of reperfusion in the in-vivo rat model. Densitometric analysis of western blots confirmed elevated levels of HSP70 in rat hearts treated with a thermal probe. There was a 9.6 and 5.4 fold increase in HSP70 expression in left and right ventricular samples, respectively, from hearts treated with local heating over untreated controls. Rats were allowed to recover for 4 hours after heat treatment to allow sufficient time for production of HSPs (Currie and White, 1983).

METHODS

Thermal Probe

In order to produce regional elevation of HSP70 in the heart a thermal probe was constructed. The probe consisted of a 6 cm long stainless steel tube (diameter=4.0 mm) with a highly conductive synthetic diamond window (surface area=12.5 mm$^2$) at the distal end and connections for circulation of water through the probe at the proximal end. Heated water from a temperature-controlled water bath was circulated through the probe to maintain the temperature between 42.5–43.5° C. at the tip of the probe. Localized hyperthermia was achieved by conductive heating from the thermal probe placed directly on the epicardial surface of the heart.

Experimental Protocol 35 male Sprague-Dawley rats (weight 300–350 g) were entered into the study. The rats were divided into 3 experimental groups with protocol end points of either HSP analysis or infarct size assessment. All rats were anesthetized with Ketamine (100 mg/kg) and Xylazine (40 mg/kg) given IP, intubated, and mechanically ventilated with 1–2% Halothane. A left thoracotomy was performed through the fifth intercostal space to expose the epicardial surface of the left ventricle. Heat-group animals (H; n=14) were treated with local applications of heat at two adjacent sites on the anterior left ventricle wall for 15 minutes each. Throughout these experiments the probe temperature was maintained in the range of 42.5–43.5° C. In sham operated control animals (C1; n=13) there was no intervention, but the chest was left open for 30 minutes. An additional control group (C2; n=6) was subjected to two local applications of the thermal probe at 37° C. (body temp) for 15 minutes each to control for any HSP70 expression mechanically induced by application of the thermal probe. The thoracotomy was closed and air was evacuated from the chest using a 20 gauge IV catheter connected to a 5 ml syringe. The rats were allowed to recover and returned to their cages. Four hours later the rats were reanesthetized and randomized to undergo either (1) 30 min. regional ischemia and 120 min. reperfusion or (2) analysis of HSP70 expression. All studies were approved and conducted within the guidelines of the animal care and use committee at the University of Texas Medical Branch, Galveston, Tex.

Ischemia/Reperfusion Protocol

A total of 19 rats (H=9, C1=10) were enrolled in the I/R protocol. Animals were mechanically ventilated as above and a midline sternotomy was performed exposing the entire heart. The left anterior descending (LAD) coronary artery was isolated at about 1 cm from its origin. Using a RB-2 taper needle, a 6.0 polypropylene stitch suture was passed beneath the artery and placed within a reversible snare occluder. The snare was tightened closing the artery and rendering a portion of the left ventricle ischemic. Occlusion of the artery was confirmed by an increase in the amplitude of the ECG as well as cyanosis of the area at risk. At 30 minutes the snare was loosened and the artery reperfused. After 120 minutes of reperfusion the animal was sacrificed and its heart excised. The aorta was cannulated and the heart was briefly perfused retrogradly with saline to wash away excess blood. The stitch suture surrounding the coronary artery was then retied and 0.8–1.0 ml of phthalocyanine blue dye was injected and allowed to perfuse the non-ischemic portions of the heart. The heart was then sliced transversely into cross sections of 2-mm thickness. Samples were photographed for measurement of area at risk (area not stained by blue dye) and then incubated in triphenyltetrazolium chloride (TTC) for 8 minutes at 37° C. to delineate infarcted from normal tissue (Vivaldi et al. 1985). Samples were fixed in 10% buffered formalin solution for 24 hours and rephotographed for measurement of infarct area (area not stained by TTC). Pictures were projected and planimetry was used to determine the area of risk expressed as a percent of left ventricle and the infarct size expressed as a percent of area of risk.

Heat-shock Protein Analysis

A total of 16 rats (H=6, C1=4, C2=6) were used for analysis of HSP70 expression. After four hours recovery, hearts from treated and untreated rats were excised, divided along the intraventricular septum into right and left ventricle, snap frozen, and stored at −80° C. Additionally, one heart from a control animal with no prior surgery was used to determine baseline HSP70 content.

Western blot analysis was used to determine HSP70 content in all myocardial samples. Tissues were weighed and diced into small slices with a razor blade. The slices were thawed in 3 ml/mg cold lysis buffer (1% Nonidet P-40, 0.5% sodium deoxycholate, 0.1% SDS, 100 μg/ml phenylmethylsulfonyl fluoride, 100 μg/ml Aprotinin, 1 mmol/L sodium orthovanadate in PBS). Tissues were homogenized with a Polytron Homogenizer (Kinematica AG, Littau, Switzerland) and stored on ice for 30 minutes. Following centrifugation at 15000×g for 20 minutes at 4° C. the supernatant was removed and centrifuged again. Protein concentration of the total cell lysate was determined with a Bradford Assay solution (Bio Rad). Equal amounts of cellular proteins (2 μg) were resolved by electrophoresis on a 0.1% SDS, 12% polyacrylamide gel (SDS-PAGE) under denaturing conditions. The proteins were transferred electrophoretically to a nitrocellulose membrane (Hybond, Amersham Corp). After blocking in 10 mM tris HCL (pH=8.0), 150 mmol/L sodium chloride and 5% (w/v) nonfat dry milk, the membranes were treated with primary antibody which recognizes the constitutive HSC70 and the inducible HSP70, for 90 minutes followed by incubation with peroxidase-conjugated secondary antibody for 45 minutes. The immune complexes were detected using a chemoluminescence reagent kit (Amersham Co., Arlington Heights, Ill.).

Statistics

All values are expressed as mean±SEM. Comparisons between heat-treated and control animals were assessed by the unpaired t test. Statistical significance was defined as $p<0.05$.

RESULTS

The thermal probe was successfully applied to the left ventricle of heat treated animals at two adjacent sites for 15 minutes each. There was no evidence of thermal injury to the epicardial surface of the heart after application of the probe. Additionally, no complications resulted from application of the thermal probe to the surface of the heart. All animals recovered successfully from the first surgical procedure and were awake within 20 minutes after closure of the thoracotomy. One (H) group animal was excluded from the infarct analysis due to damage to the coronary artery during the I/R protocol preventing adequate reperfusion. Two (C1) animals died before completion of the infarct analysis protocol during reperfusion and were excluded from further analysis.

Infarct Size Analysis

Figure 6A:
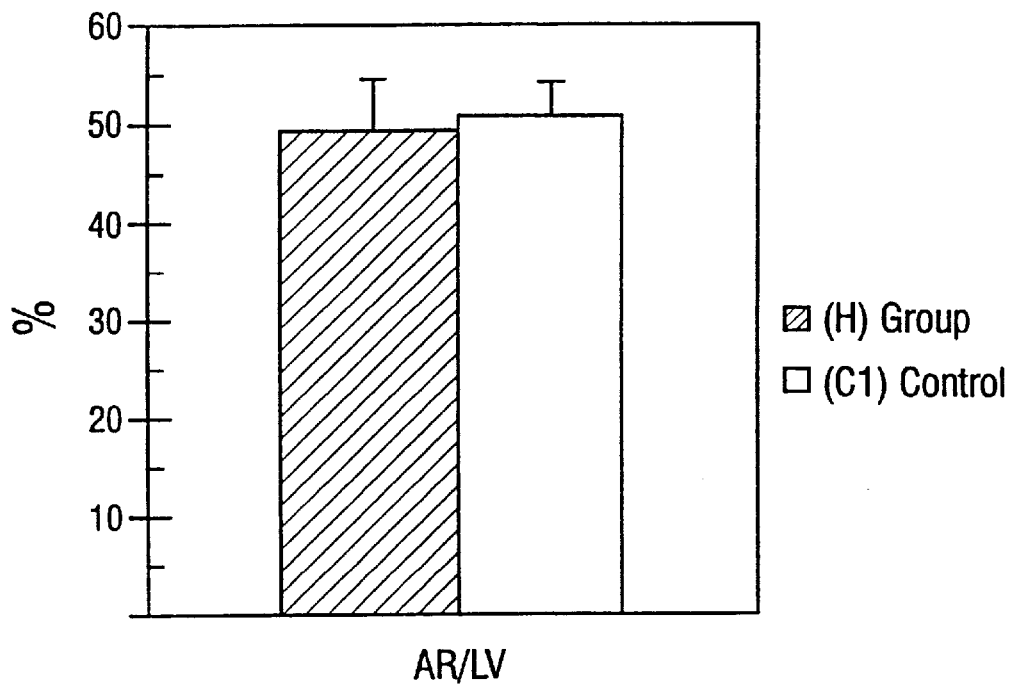
FIG. 6A. Bar graphs showing resulting area at risk in the left ventricle in heat treated rats (hashed bar) and controls (solid bar) after 30 minutes of regional ischemia and 2 hours of reperfusion. No difference is seen in area at risk as a percentage of left ventricle in either group.
Figure 6B:
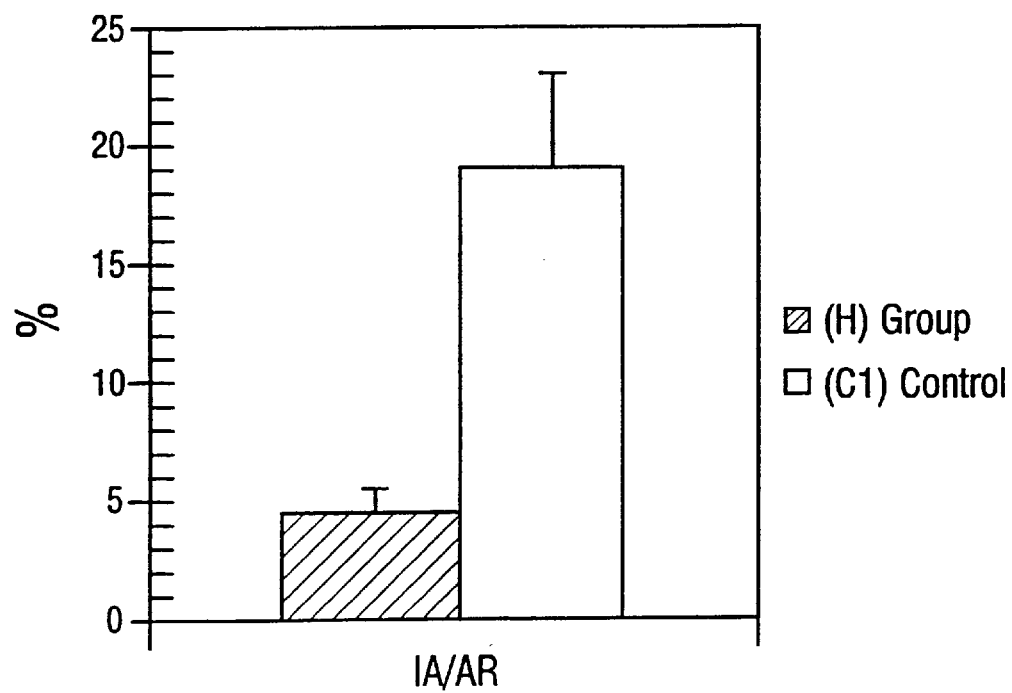
FIG. 6B. Bar graphs showing resulting infarct sizes in heat treated rats (hashed bar) and controls (solid bar) after 30 minutes of regional ischemia and 2 hours of reperfusion. Compared to controls, heat treated rats demonstrated a significant ($p<0.005$) reduction in infarct size expressed as a percentage of area at risk.

Table 1. summarizes the results from animals that underwent the infarct analysis protocol. There was no significant difference in the area at risk (expressed as a percent of left ventricular area) as a result of LAD coronary occlusion in (H) group and (C1) group animals (49.5±5.4% vs 51.5±3.5%; mean±SEM)(FIG. 6A). However, rats treated with two local applications of heat using the conductive thermal probe demonstrated a marked decrease in infarct size. Localized heat stress resulted in a significant ($p<0.005$) limitation of infarct size expressed as a percentage of area at risk in heat treated animals vs controls (4.26±0.85 vs 19.2±3.4%)(FIG. 6B).

Table 1. Infarct sizes of heat-treated and control rats after 30 minutes of ischemia and 120 minutes of reperfusion.

| Group | AR/LV (%) | IA/AR (%) |
|---|---|---|
| Heat Group (H; n = 8) | 49.5 ± 5.4 | 4.26 ± 0.85* |
| Control Group (Cl; n = 8) | 51.5 ± 3.5 | 19.2 ± 3.4 |

*($p < .005$ vs control (Cl))

Figure 7:
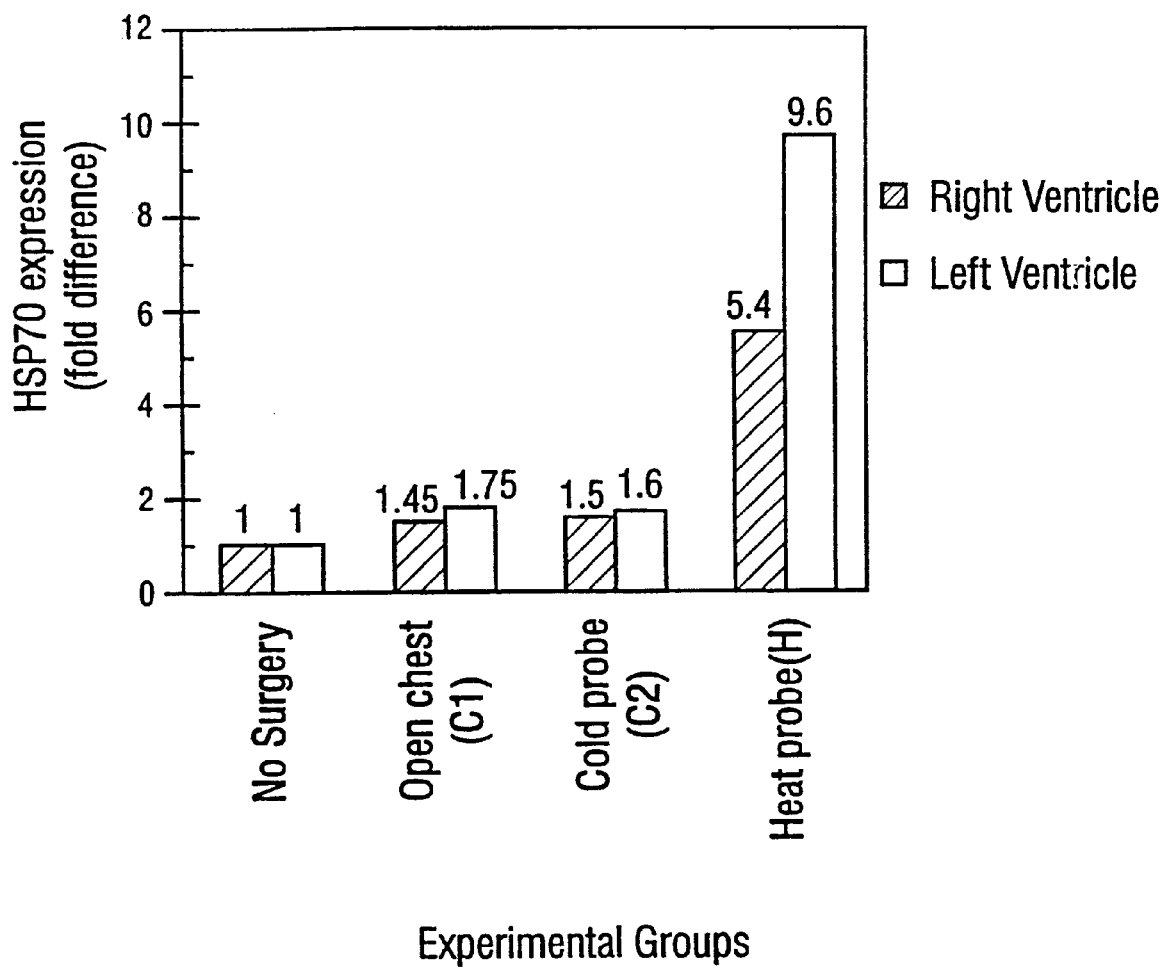
FIG. 7. Bar graphs showing gel densitometric analysis of immunoblots indicating levels of HSP70 expression, from right and left ventricular samples of four groups of rats, from left to right, no surgery, open chest (C1), cold probe (C2) and heat probe (H). Hatched bars are right ventricle and solid bars are left ventricle. Values are fold difference compared to "no surgery" controls. Local heat application increased heat shock protein 70 expression in both right (non-treated) and left (treated) ventricles when compared with either control. HSP elevations were higher in heated regions (LV) compared to non-heated (RV) in (H) group animals while no significant difference was observed between LV and RV samples from controls.

AR/LV (%)—Area at risk as a percentage of left ventricular area IA/AR (%)—Infarct area as a percentage of area at risk Group (H)—Two local applications of heat (42.5–43.5° C.) for 15 minutes Control (C1)—Sham operated control (30 minutes open chest)
HSP70 Analysis Western Blot analysis confirmed elevation of HSP70 in rats treated with the thermal probe in both right and left ventricular samples. There was not an appreciable difference noticed in the expression of HSP70 in either control group (C1 or C2). Gel densitometric analysis of immunoblots showed a marked difference in the expression of HSP70 between heat-treated animals and controls. There was a 5.4 and 9.6 fold difference in right and left ventricular samples respectively between heat treated animals and a control animal that had no prior surgery. Both control groups showed only a small increase in HSP70 expression when compared to the same control animal with no prior surgery (1.5 fold increase) (FIG. 7).

EXAMPLE 4

Effect of Laser Irradiation on Potentially Arrhythmic Tissue Following Injury or During Remodeling The myocyte hypertrophy and increased intracellular collagen that occurs during infarct healing and remodeling are associated with life-threatening ventricular arrhythmias. The present device may be used to influence the degree of local hypertrophy and collagen formation (or collagen breakdown) by directly changing relevant proteins or their genetic expression. Thus the present device may aid in the study of, or therapeutically change how tissue responds to injury.

EXAMPLE 5

Use of Intramyocardial Electrograms as an Adjunct to Endocardial Mapping and Guide to Intramyocardial Coagulation An embodiment of the present invention is the use of the apparatus described herein for recording intramyocardial electrograms, i.e. the electrical activity located within the ventricular wall. The tissue in this region is frequently critical for the maintenance of sustained ventricular arrhythmias.

In the practice of the present example, intramyocardial electrograms assist with the mapping that precedes arrhythmia ablation. When the outer catheter is in the desired position a wire is advanced down the central lumen and into the tissue. The intramyocardial segment of the wire must be capable of recording intramyocardial electrical activity. This is achieved by incorporating electrodes into the segment. Simultaneous surface recordings are made using the distal electrode(s) of the outer catheter, which would be in contact with tissue.

Once this information has been obtained, the wire is removed and exchanged for the diffusion tipped laser fiber optic, which is positioned within the myocardium at the same location. Alternatively, the wire may be positioned within the tissue after it is coagulated to confirm necrosis and measure its depth. This assessment of tissue viability is considered Example 6.

EXAMPLE 6

Assessment of Tissue Composition Using Intramyocardial Electrograms and Associated Optical Properties Disease affecting the myocardium, such as scarring from healed infarction, inflammation, and infiltrative disorders (amyloid, sarcoid), change tissue composition and in so doing will alter the appearance of the intramyocardial electrogram and the optical properties of the tissue. The optical and electrical changes may be evaluated singly or correlated to recognize the location, type, and extent of tissue involvement.

The mapping information reveals the best location for endomyocardial biopsy, which can be missed when the disease process is patchy or local. The data could also determine the color, and thus the absorptive properties of the tissue, which may help in selecting the laser wavelength most appropriate for an intended task (e.g. coagulation).

EXAMPLE 7

Non-Lethal Modification of Tissue Electrophysiology Using Photodynamic Therapy (PDT) to Alter Select Cellular Proteins or Genetic Loci The devices of the present invention may also be used for techniques or methods that can be considered a form of non-lethal arrhythmia "ablation." Labeling potassium, calcium, or sodium channels (or agents that bind to them) with light activated substances may selectively and locally modify electrical conduction after laser irradiation. Alternatively these proteins may be altered by irradiating the gene responsible for their expression.

EXAMPLE 8

Induction of Cellular Apoptosis

Apoptosis is a phenomenon whereby cells sometimes appear programmed to die and do so without apparent cause or resulting inflammation. The process occurs in utero, when tissues are necessarily resorbed in the course of their morphologic development. The process may also continue after birth and cause pathologic tissue loss.

Certain cardiac disorders that result from localized hypertrophy (most notably hypertrophic obstructive cardiomyopathy) may be treated by surgical removal of the exuberant tissue. The present device may be used to induce apoptosis in these regions when the appropriate proteins or gene loci are identified, labeled and irradiated.

While the apparatus and methods of this invention have been described in terms of preferred embodiments, it will be apparent to those of skill in the art that variations may be applied to the apparatus and methods described herein without departing from the concept, spirit and scope of the invention. All such variations and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Currie, R. W. and White, F. P., Characterization of the synthesis and accumulation of a 71-kilodalton protein induced in rat tissues after hyperthermia. *Can. J. Biochem. Cell Biol*, 1983; 61:438–446.

Currie, R. W., Karmazyn, M., Malgorzata, K., and Mailer, K., Heat-Shock response is associated with enhanced postischemic ventricular recovery. *Circulation Research*, 1988; 63:543–549.

Currie, R. W., Tanguay, R. M., and Kingma, J. G., Heat-Shock response and limitation of tissue necrosis during occlusion/reperfusion in rabbit hearts. *Circulation*, 1993; 87:963–971.

Donnelly, T. J., Sievers, R. E., Vissern, F. L. J., Welch, W. J., and Wolfe, C. L., Heat shock protein induction in rat hearts. A role for improved myocardial salvage after ischemia and reperfusion? *Circulation*, 1992; 85:769–778.

Hutter, M. M., Sievers, R. E., Barbosa, V. B., and Wolfe, C. L., Heat-shock protein induction in rat hearts. A direct correlation between the amount of heat-shock protein induced and the degree of myocardial protection. *Circulation*, 1994; 89:355–360.

Vivaldi, M. T., Kloner, R. A., and Schoen, F. J., Triphenyltetrazolium staining of irreversible ischemic injury following coronary artery occlusion in rats. *Am J Path*, 1985; 121:522–530.

Walker, D. M., Pasini, E., Kucukoglu, S., Marber, M. S., Iliodromitis, E., Ferrari, R., and Yellon, D. M., Heat stress limits infarct size in the isolated perfused rabbit heart. *Cardiovascular Research*, 1993; 27:962–967.

Yellon, D. M., Pasini, E., Cargnoni, A., Marber, M. S., Latchman, D. S., and Ferrari, R., The protective role of heat stress in the ischemic and reperfused rabbit myocardium. *J Mol Cell Cardiol*, 1992; 24:895–908.

What is claimed is:

1. A method of inducing angiogenesis comprising the steps of:
   (a) positioning the distal end of a catheter proximate to the endocardium;
   (b) identifying a target area of tissue;
   (c) extending the distal end of a conductor through the distal end of the catheter and into the tissue; and
   (d) transmitting energy through the conductor into the tissue to create volumetric hyperthermia in said tissue.

2. The method of claim 1, wherein the conductor comprises a wave guide and the energy comprises laser energy.

3. The method of claim 1, wherein said tissue reaches a temperature of at least about 40° C.

4. The method of claim 1 wherein said energy is conductive energy.

5. A method of inhibiting tissue damage due to ischemia comprising providing radiative or conductive energy within said tissue in an amount effective to induce local volumetric hyperthermia.

6. The method of claim 5, wherein said tissue is heart tissue and said energy is applied beneath the endocardial surface, beneath the epicardial surface or within the interstitial area of said heart.

7. A method of inhibiting tissue damage due to insults including reperfusion injury, said method comprising providing radiative or conductive energy within said tissue in an amount effective to induce local volumetric hyperthermia.

8. The method of claim 7, wherein said tissue is heart tissue and said energy is applied beneath the endocardial surface, beneath the epicardial surface or within interstitial area of a heart.

9. The method of claim 7, wherein said tissue comprises an organ and the energy is applied in vivo or in vitro to said organ in order to extend the time for tissue transplant and/or to improve the outcome of organ transplant.

10. A method for the endogenous production of heat shock proteins (HSPs) or growth factors within tissue comprising:
   delivering energy into the tissue to create volumetric hyperthermia in said tissue in an amount effective to stimulate the expression and release of HSPs or growth factors within the tissue.

11. The method of claim 10, wherein the tissue is cardiac tissue.

12. The method of claim 10, wherein HSP70 is produced in the tissue.

13. The method of claim 10, wherein vascular endothelial growth factor (VEGF) is produced in the tissue.

14. The method of claim 10, wherein the tissue is cardiac tissue and the energy is delivered by penetrating the endocardium and applying said energy to the myocardium.

15. The method of claim 10, wherein the energy is delivered interstitially.

16. The method of claim 10, wherein the tissue is heated to a temperature of greater than 40° C.

* * * * *